United States Patent [19]
Fisher et al.

[11] Patent Number: 5,490,854
[45] Date of Patent: Feb. 13, 1996

[54] SURGICAL CUTTING BLOCK AND METHOD OF USE

[75] Inventors: Michael G. Fisher, Eldorado Hills, Calif.; Joe Nemeth, Saint Albans, Vt.

[73] Assignee: Synvasive Technology, Inc., Rancho Cordova, Calif.

[21] Appl. No.: 107,468

[22] Filed: Aug. 17, 1993

Related U.S. Application Data

[63] Continuation-in-part of Ser. No. 838,486, Feb. 20, 1992, abandoned.

[51] Int. Cl.⁶ .......................... A61B 17/15; A61B 17/56
[52] U.S. Cl. ................... 606/88; 606/86; 606/79; 606/82
[58] Field of Search ................ 51/307, 308, 309; 83/658; 148/407, 421; 501/127; 606/79, 82, 86–89, 53, 76

[56] References Cited

U.S. PATENT DOCUMENTS

| | | | |
|---|---|---|---|
| 707,294 | 8/1902 | Blackhall . | |
| 1,696,834 | 12/1928 | Brodfuehrer et al. . | |
| 2,618,567 | 11/1952 | Comstock | 501/127 X |
| 2,621,691 | 12/1952 | Brualdi | 146/78 |
| 3,025,175 | 3/1962 | Aldred | 501/127 X |
| 3,148,981 | 9/1964 | Ryshkewitch | 501/127 X |
| 4,587,225 | 5/1986 | Tsukama et al. | 501/127 |
| 4,668,644 | 5/1987 | Filholl | 501/127 |
| 4,718,413 | 1/1988 | Johnson | 128/92 |
| 4,759,350 | 9/1988 | Dunn et al. | 128/92 |
| 4,820,666 | 4/1989 | Hirano et al. | 501/104 |
| 4,892,093 | 1/1990 | Zarnowski et al. | 606/82 |
| 4,952,213 | 8/1990 | Bowman et al. . | |
| 5,053,037 | 10/1991 | Lackey | 606/79 |
| 5,092,869 | 3/1992 | Waldron | 606/82 |
| 5,100,408 | 3/1992 | Lackey | 606/79 |
| 5,122,144 | 6/1992 | Bert et al. | 606/87.88 |
| 5,129,909 | 7/1992 | Sutherland . | |
| 5,152,794 | 10/1992 | Davidson | 623/16 |
| 5,250,050 | 10/1993 | Poggie et al. | 606/79 |

OTHER PUBLICATIONS

European Patent Aplication NO. 0 243 109, Dow Corning Wright, Filed Apr. 16, 1987.

Primary Examiner—Robert A. Hafer
Assistant Examiner—Brian E. Hanlon
Attorney, Agent, or Firm—F. Michael Zarrabian; Sheldon & Mak, Inc.

[57] ABSTRACT

An improved surgical cutting block for guiding bone saws in joint surgery and similar instruments. The cutting block is provided with one or more cutting guides having cutting guide surfaces positioned on exterior faces of the block or along channels within the block. The cutting guide surface is formed of a material having a Knoop hardness of 466 or greater (under a 500 gm load or greater), a chrome content of less than 10% and a nickel content of less than 4%. According to another aspect of the invention, a method of cutting bone tissue utilizing the improved surgical cutting device is disclosed wherein heat-generated damage to bone tissue is reduced and production of toxic residue is minimized.

12 Claims, 2 Drawing Sheets

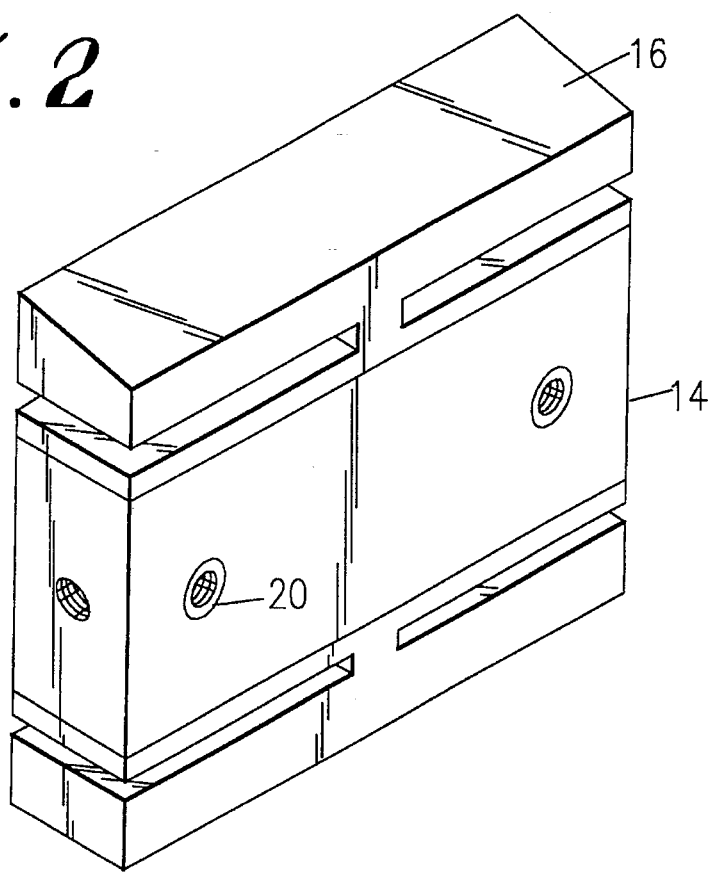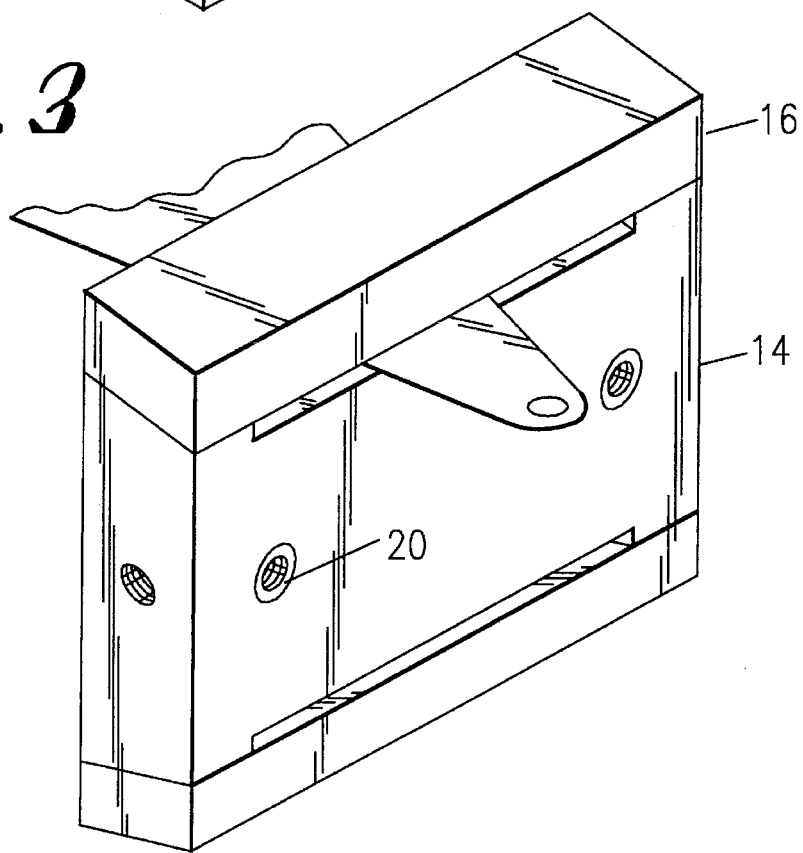

[5,490,854]

SURGICAL CUTTING BLOCK AND METHOD OF USE

The present application is a continuation-in-part of U.S. patent application Ser. No. 07/838,486, filed Feb. 20, 1992 now abandoned.

FIELD OF THE INVENTION

The field of the invention relates to surgical devices, and more particularly to surgical cutting blocks used for guiding saws and similar cutting devices in the shaping of bone, cartilage and similar tissue.

REFERENCE

Sunderman et al. 1989. Journal of Orthopaedic Research 7:307–315.

BACKGROUND OF THE INVENTION

Artificial joints, such as knee and hip socket replacements, are frequently implanted in the body to repair or replace damaged or diseased joints. In order to achieve a successful implant, the bone adjacent to the joint must first be cut and shaped in a configuration that is geometrically reciprocal to the shape of the implant, Typically, surgeons cut with a saw blade attached to a motorized surgical handpiece that propels the blade in a variety of directional or bi-directional motions.

In most joint replacement surgery, the fit between the bone surface and the replacement must be very precise, often within tolerances of a few thousands of an inch. Virtually all surgeons use a cutting block to hold captive or guide a blade along a reference cutting surface along one or more sides of the cutting block. The reference cutting surface assures that the cutting plane will be extended to and through the bone by helping guide the blade on its path through the bone.

Although widely used, known cutting blocks and surgical methods based on the use of known cutting blocks suffer from several serious problems. A commonly encountered problem is systemic toxicity following surgery. Standard surgical cutting blocks are fabricated from various grades of stainless steel that are quickly eroded by the high speeds at which most surgical blades operate. The result of such erosion is the production of a slurry, commonly referred to as "sludge," in and near the operation site. The sludge contains the various elements present within the steel alloy of both the cutting block and the surgical saw blade. A number of metals often found in stainless steel alloys, most notably chrome and nickel, are left behind in the joint and eventually make their way throughout the patient's body. Nickel is particularly toxic and is a known carcinogen. In a recent study, Sunderman et al. (1989) report that nickel concentrations in patients having joint replacement surgery rose 11 fold in the 1 to 2 days following surgery, as compared with pre-operative levels.

Aside from the problem of toxic sludge, erosion of the stainless steel cutting blocks quickly causes fretting of the reference cutting surface, thereby destroying the ability of the cutting block to provide a precise reference plane during surgery. In most applications, tolerances of a few thousandths of an inch are lost after 5 to 10 minutes of cutting, thereby forcing the surgeon to replace the cutting block (often impractical during surgery) or accept a less precise cut. Unfortunately, the failure to provide a precise alignment along the surface contact between the prosthesis and the remaining bone can result in post-operative bone degradation, infection and joint failure.

Another serious problem associated with known cutting blocks is the heat of friction created during surgery. Although heat is generated by the frictional interaction of the saw blade and the bone, a substantial amount of heat is nevertheless generated by frictional contact between the saw blade and the cutting block. It is well known that damage to bone tissue begins after bone temperature exceeds 50° C. and that irreparable damage takes place after temperatures exceed 70° C. for three or more minutes. Known cutting devices and methods can generate temperatures in excess of 50° C. or even 70° C.

In view of the foregoing, there is a clear need for a surgical cutting block and method of use that substantially reduces or eliminates delivery of toxic elements to a patient as a by-product of erosion of the cutting block. There is also a need for a cutting block with superior hardness that is capable of retaining its original configuration without unacceptable fretting during prolonged use. A further need is for a cutting block and blade combination that has a relatively low coefficient of friction during operation, thereby reducing blade heating and bone tissue degradation.

SUMMARY OF THE INVENTION

It is therefore a general object of the invention to provide an improved cutting block having a reference surface formed of a composition that has minimal amount of toxic and carcinogenic elements such as nickel and chrome.

It is another object of the present invention to provide a cutting block having a cutting guide surface that has a relatively low coefficient of friction when used in surgery with a given blade whereby heat build up in the blade from frictional contact with the cutting guide surface is minimized.

Still another object of the invention is to provide a method for cutting bone and similar hard tissue that does not leave behind toxic by-products at the operation site.

Another object of the invention is to provide a method of cutting bone and similar hard tissue that is capable of making a precise cut with a desired tolerance of a few thousands of an inch.

A further object of the invention is to provide a method of cutting bone or similar hard tissue that minimizes heat damage to bone tissue.

Another object of the invention is to provide a method for precision cutting of hard tissues that does not result in deposit of toxic substances in the body or result is heat-associated tissue damage.

The invention meets these objects by providing an improved cutting block having one or more cutting guide surfaces formed from a composition having a Knoop hardness of 466 or greater (under a 500 gm load or greater), a chrome content of less than 10% by weight and a nickel content that is less than 4% by weight.

The cutting block of the invention may be entirely composed of the desired composition or may be a composite construction having a core unit composed of stainless steel or other material suitable for surgical applications that is fitted with and coupled to one or more subunits fabricated from the composition described above and configured with a desired cutting guide surface. Such units may be discrete blocks that are physically affixed to or inlaid into a desired surface of the core unit or alternatively may comprise coatings or deposits that are bonded to a desired surface of the core unit using known techniques.

The method of the invention meets these objects by utilizing the cutting block of the invention in concert with stainless steel blades or blades of other compositions having the hardness and chemical composition characteristic of the cutting guide surface.

The surgical device and method of the invention are advantageous over prior art in that toxic deposits within the joint as a result of surgery are minimized, or entirely eliminated; in that the tolerances of the reference cutting surface are maintained throughout surgery; and in that blade heating due to friction between the blade and cutting guide surface is significantly reduced.

These and other objects and advantages of the invention will become more fully apparent when the following detailed description of the invention is read in conjunction with the accompanying drawings.

BRIEF DESCRIPTION OF THE DRAWINGS

FIG. 2 is a view in perspective of a first saw-captive embodiment of the cutting block of the invention.

FIG. 3 is a view in perspective of a second saw-captive embodiment of the cutting block of the invention.

DETAILED DESCRIPTION OF THE INVENTION

Figure 1A:
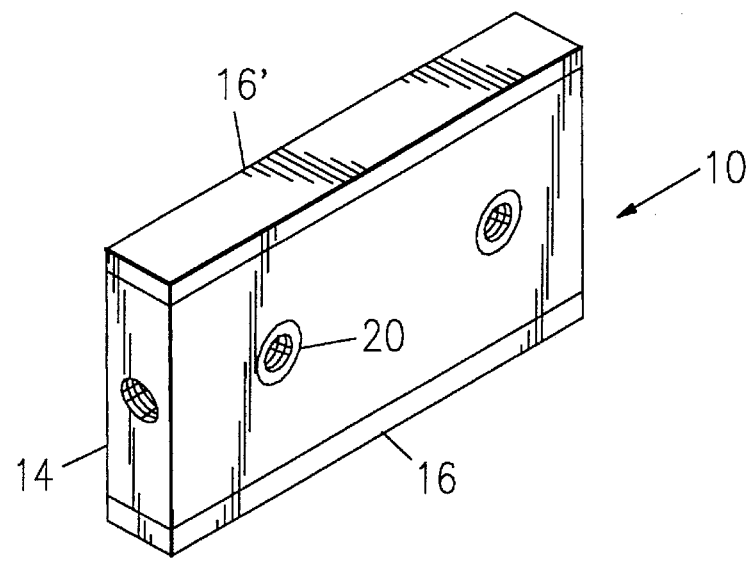
FIGS. 1A & 1B are views in perspective of two embodiments of the cutting block of the invention.
Figure 1B:
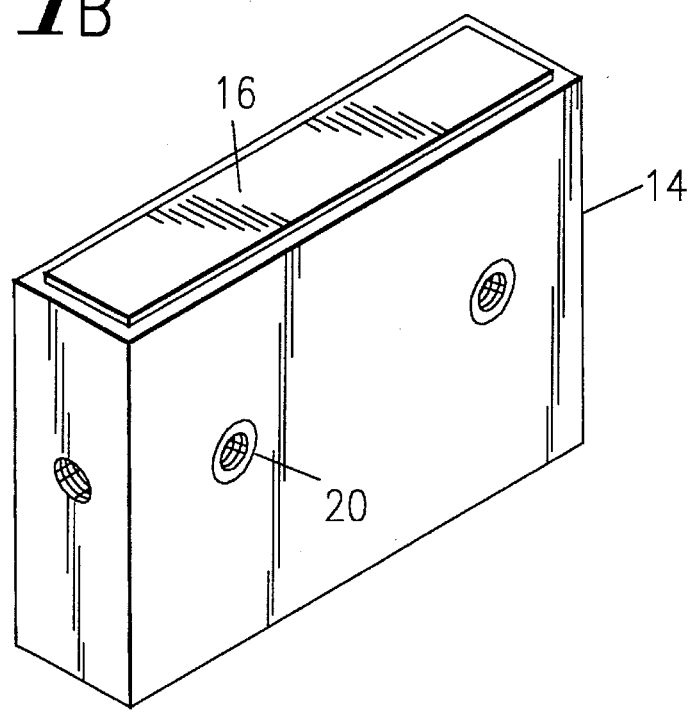

Cutting Block Structure. Turning now to the figures, the cutting block and the invention will now be described. According to one embodiment of the invention, cutting block 10 can be comprised of a single material or composition that has been shaped to provide one or more cutting guide surfaces 12. Alternatively, as shown in FIG. 1A and 1B, cutting block 10 may be comprised of a core unit 14 coupled to one or more cutting guide units 16. Additionally, cutting block 10 can be provided with positioning pins 18 that are either integral with the cutting block or are attached to the cutting block via holes 20.

Although cutting blocks with cutting guide surfaces positioned on one or more outside faces are suitable for all types of orthopaedic surgery, saw-captive blocks are preferred by some surgeons. According to another embodiment of the invention, saw-captive cutting blocks are depicted in FIGS. 2 and 3. Cutting block 10 may be configured to provide open channels extending laterally from each end, as shown in FIG. 2 or may be provided with internal channels as shown in FIG. 3. In each case, the block may be comprised of a solid piece of material having the desired hardness and metal content characteristics, or may be a composite comprised of a core unit 14 coupled with cutting units 16 so that the cutting guide surfaces 12 are comprised of a desired material.

Cutting Guide Surface Fabrication Materials. Although the composition of the interior portion of the block and positioning pins can be of almost any durable, hard material that is not easily fractured, such as stainless steel, the cutting guide surface 12 of the cutting block should be of a material having a high degree of hardness coupled with low chrome and low nickel content. Satisfactory parameters for such a material include a Knoop hardness of 466 or greater (under a 500 gm load or greater), a chrome content of less than 10% and a nickel content of less than 4%. A preferred material would have a Knoop hardness of 800 or greater (under a 500 gm load or greater), a chrome content of less that 8% and a nickel content of less that 3%. A most preferred material would have a Knoop hardness of 1000 or greater (under a 500 gm load or greater), a chrome content of less than 6% and a nickel content of less than 2%.

One class of materials having the desired characteristics that would be suitable for a cutting guide surface are ceramics. Ceramics have a high strength to weight ratio, are corrosion resistant, have a high chemical inertness and are very wear resistant. Furthermore, ceramics can be fashioned to be entirely free of chrome and nickel. Suitable ceramics include oxides, carbides, nitrides and borides of various cationic elements.

Useful oxide ceramics principally include alumina and zirconia, and in particular magnesia and ceria stabilized zirconia, which share many of the same characteristics, except that ceria stabilized zirconia has a considerably higher fracture toughness. Oxide ceramics include any cation of atomic number three or greater combined with an anion of oxygen. Generally, alumina and zirconia are most suitable. However, small amounts of other oxides may be blended with alumina or zirconia to form homogeneous compositions. Characteristics of exemplary oxide ceramics are specified in Table I.

Carbide ceramics are also suitable for use in fabrication cutting reference guides in the cutting block of the invention. The most important of these are silicon and boron carbide, as well as the more conventional tungsten carbide. The latter is frequently termed carbide tool steel, but by

TABLE I

GENERAL TECHNICAL SPECIFICATIONS OF OXIDE CERAMICS

| Property | Units | Alumina 96% | Alumina 99.5% | Zirconia Magnesia Stabilized |
| --- | --- | --- | --- | --- |
| Density | g/cc | 3.75 | 3.9 | 5.60 |
| Flexual Strength | kpsi* | 52 | 55 | 70 |
| Compressive Strength | kpsi | 300 | 380 | 250 |
| Hardness | Knoop | 1080 | 1450 | 1000–1200 |
| Modulus of Elasticity | Mpsi⁺ | 44 | 54 | 29 |
| Coefficient of Friction | | 0.10 (lubed) | 0.10 (lubed) | <0.15 (lubed) <0.5 (non-lubed) |

*K = 1,000
⁺M = 1,000,000 definition is a ceramic material. Important characteristics of selected carbide ceramics are summarized in Table II.

TABLE II

GENERAL TECHNICAL SPECIFICATIONS OF CARBIDE CERAMICS

| Property | Units | Silicon Carbide | Boron Carbide | Tungsten Carbide |
| --- | --- | --- | --- | --- |
| Density | g/cc | 3.1 | 2.5 | 15 |
| Flexual Strength | kpsi* | 100 | 51 | 300 |
| Compressive Strength | kpsi | 300 | 400 | 600 |
| Hardness | Knoop | 2500 | 3000 | 1550 |
| Modulus of Elasticity | Mpsi⁺ | 70 | 60 | 75 |
| Coefficient of Friction | | 0.10 (lubed) | 0.10 (lubed) | <0.10 (lubed) |

*K = 1,000
⁺M = 1,000,000

As with oxide ceramics, carbide ceramics can be formed from blends of carbides together, or even as blends of carbides with other classes of ceramics, such as oxides.

Another class of suitable ceramics include the nitrides, most notably silicon nitride, aluminum nitride and titanium nitride. Important characteristics of exemplary nitride ceramics are summarized in Table III.

TABLE III

GENERAL TECHNICAL SPECIFICATIONS OF NITRIDE CERAMICS

| Property | Units | Silicon Nitride | Aluminum Nitride |
|---|---|---|---|
| Density | g/cc | 3.2 | 3.3 |
| Flexual Strength | kpsi* | 70 | 45 |
| Compressive Strength | kpsi | 300 | |
| Hardness | Knoop | 1900 | 1180 |
| Modulus of Elasticity | Mpsi+ | 40 | 45 |
| Coefficient of Friction | | <0.08 (lubed) | <0.08 (lubed) |

*K = 1,000
+M = 1,000,000

Finally, borides also form ceramics suitable for use in the cutting guide surface of the invention. Most notable among these are titanium diboride and zirconium diboride. The former is notable in its extreme Knoop hardness, the latter exceptional in its corrosion and oxidation resistance. Properties of selected borides are summarized in Table IV.

All ceramics listed above can be obtained from a number of ceramics manufacturers, most notably Coors Ceramic Company (Golden, Colo.), Kyocera Co., and 3M Ceramics (St. Paul, Minn.). Of these ceramics, zirconia and alumina, as well as zirconia-alumina blends are most preferred in that they are relatively inexpensive to manufacture and have the advantageous hardness, wear resistance and very low heavy metal content desired in a cutting reference guide material. In any event, the desired ceramic material of the invention is fabricated as a substantially homogenous composition. To the extent that a desired ceramic is comprised of more than one cation and/or more than one anion, then the various components are very finely blended to produce a substantially homogeneous composition.

In addition to the typical ceramic compounds discussed above, ceramic composites developed by infiltration techniques are also suitable. Such ceramics are formed by

TABLE IV

GENERAL TECHNICAL SPECIFICATIONS OF BORIDE CERAMICS

| Property | Units | Titanium Diboride | Zirconium Diboride |
|---|---|---|---|
| Density | g/cc | 4.48 | 6.09 |
| Flexual Strength | kpsi* | 45 | |
| Compressive Strength | kpsi | | |
| Hardness | Knoop | 2500–3000 | 1560 |
| Modulus of Elasticity | Mpsi+ | 75 | 30 |
| Coefficient of Friction | | | |

*K = 1,000
+M = 1,000,000 wicking molten metal through a porous ceramic preform matrix. The metal reacts with the ceramic and forms an intimate chemical-mechanical bond, literally being drawn through its own oxidation product to sustain the infiltration and growth process. Examples of such compositions are given in Table V. Such ceramic composites may be obtained from Lanxide Company.

Aside from ceramics of various sorts, other materials that are low or lacking in nickel and chrome, but which possess the desired hardness and wear characteristics, are suitable for use in fabricating cutting references guides in the cutting block of the invention. These include nitrided titanium and nitrided cobalt chrome alloys obtained from known techniques of diffusing nitrogen into the metal surface under high or low gas pressures, or through plasma-based techniques. Also suitable are high molecular weight and ultra high molecular weight polyethylene plastic, obtainable from both DuPont and G.E. Plastics.

TABLE V

EXAMPLES OF COMPOSITES MADE BY INFILTRATION PROCESS

| Matrix | Reinforcing Filler |
|---|---|
| Aluminum Oxide | Aluminum Oxide, Silicon Carbide Barium Titanate |
| Aluminum Nitride | Aluminum Nitride, Aluminum Oxide, Boron Carbide, Titanium Diboride |
| Zirconium Nitride | Zirconium Nitride, Zirconium Diboride |
| Titanium Nitride | Titanium Nitride, Titanium Diboride, Aluminum Oxide |

Of course, the materials set forth above can be used to fabricate whole cutting blocks where such fabrication is cost-effective. Alternatively, cutting guide units 16 fabricated from these materials can be laminated or otherwise affixed at desired positions and angles on a core unit. Further, a suitable cutting guide reference surface may be achieved by directly depositing one or more of the desired materials on a preformed cutting guide surface, so long as the thickness and durability of the deposit is sufficient to preform under normal surgical conditions.

Method of the Invention. According to another aspect of the invention, a method of precision cutting of bone, cartilage and other hard to moderately hard body tissues is provided. Typically, the surgeon will first expose the joint or joint region to be replaced. Holes will be drilled into the bone having a depth and position reciprocal to the configuration of the alignment pins of the cutting block so that the cutting guide surface of the cutting block is properly aligned to cut the bone at a desired angle and to a desired depth using a standard saw. A cutting block having a cutting guide surface composed of a material having the hardness characteristics set forth above is then emplaced into the joint by inserting the alignment pins into the bone drill holes. The surgeon then uses the cutting guide surface to align and guide the blade as a cut is made into the cartilage and bone tissue. With cutting blocks having the cutting guide surface on an external face of the block, the surgeon made place pressure on the blade during surgery to cause the blade to bow, thereby adjusting the angle of the cut as surgery proceeds. After the bone has been cut and removed, the joints prothesis is emplaced and the joint is closed. The cutting block of the invention may also be used to cut soft tissues, either using adjacent bone as a reference anchor or by using adjustable mount separate from the patient.

From the foregoing, it will be appreciated how the objects and features of the invention are met. First, the hardness of the cutting guide surface materials of the invention helps to prevent fretting, thereby maintain the plane of the reference cutting guide within the very narrow tolerances required in orthopaedic surgery.

Second, the materials are low, if not entirely lacking in, toxic metal ions that may be shed in sludge during surgery. The very low levels of chrome and nickel contribute materially to both patient recovery and prosthesis success.

Third, the hardness and lubricity the materials, particularly ceramics such as zirconia, substantially reduces friction, and thus heat generation, during an operation thereby resulting in less damage to healthy bone tissue than in known procedures.

Although the invention has been described with respect to a particular surgical cutting block and method for its use, it will be appreciated that various modifications of the apparatus and method are possible without departing from the invention, which is defined by the claims set forth below.

I claim:

1. A surgical cutting block for use in guiding bone saws and similar blades in orthopaedic surgery, comprising:

a surgical cutting block having a core unit including means for reversibly attaching the core unit to bone and soft tissue being cut in a predetermined position such that the core unit is attached to the bone and soft tissue being cut, and removed from the bone and soft tissue after cutting is completed, the core unit having at least one cutting guide surface consisting essentially of a material having a Knoop hardness of 466 or greater (under a 500 gm load), a nickel content of 0% to less than 4% and a chrome content of 0% to less than 10% said material selected from the group consisting of substantially homogenous ceramic oxides, substantially homogenous ceramic carbides, substantially homogenous ceramic borides, substantially homogenous ceramic borides, substantially homogenous ceramic nitrides, nitrogen-hardened titanium, and nitrided cobalt chrome.

2. The surgical cutting block of claim 1 wherein the material is selected from the group consisting of zirconia, alumina and nitrogen hardened titanium.

3. The surgical cutting block of claim 2 wherein the material is zirconia.

4. A surgical cutting block for use in guiding bone saws and similar blades in orthopaedic surgery, said cutting block comprising:

a) a core unit having a first end and a second end;

b) a first cutting guide unit coupled to the first end of said core unit and provided with a through channel having at least one cutting guide surface; and c) a second cutting guide unit coupled to the second end of said core unit and provided with a through channel having at least one cutting guide surface, wherein each of said cutting guide units is provided with a cutting guide surface formed of a material having a Knoop hardness of 466 or greater (under a 500 gm load), a nickel content of 0% to less than 4% and a chrome content of 0% to less than 10%, said material selected from the group consisting of substantially homogenous ceramic oxides, substantially homogenous ceramic carbides, substantially homogenous ceramic borides, substantially homogenous ceramic nitrides, nitrogen-hardened titanium, and nitrided cobalt chrome.

5. The surgical cutting block of claim 4 wherein the material is selected from the group consisting of zirconia, alumina and nitrogen hardened titanium.

6. The surgical cutting block of claim 5 wherein the material is zirconia.

7. A method of cutting bone for a receipt of a coupling surface of a joint prothesis utilizing a cutting block having at least one cutting guide surface formed upon a cutting guide for guiding bone saws and similar blades, said method comprising the steps of:

a) implanting said cutting block in a desired position on the joint; and b) cutting the bone to sculpt a surface that is geometrically reciprocal to and capable of snug receipt of the coupling surface of said joint prosthesis wherein the cutting guide surface of said cutting block is formed of a material having a Knoop hardness of 466 or greater (under a 500 gm load), a nickel content of 0% to less than 4% and a chrome content of 0% to less than 10%, said material selected from the group consisting of substantially homogenous ceramic oxides, substantially homogenous ceramic carbides, substantially homogenous ceramic borides, substantially homogenous ceramic nitrides, nitrogen-hardened titanium, and nitrided cobalt chrome.

8. The surgical cutting block of claim 7 wherein the material is selected from the group consisting of zirconia, alumina and nitrogen hardened titanium.

9. The surgical cutting block of claim 8 wherein the material is zirconia.

10. A surgical cutting block for use in guiding bone saws and similar blades in orthopaedic surgery, comprising:

a surgical cutting block having a core unit including means for reversibly attaching the core unit to bone and soft tissue being cut in a predetermined position such that the core unit is attached to the bone and soft tissue being cut, and removed from the bone and soft tissue after cutting is completed; and at least one cutting guide unit coupled to the core unit, the cutting guide unit provided with a cutting guide surface consisting essentially of a material having a Knoop hardness of 466 or greater (under a 500 gm load), a nickel content of 0% to less than 4% and a chrome content of 0% to less than 10%, the material selected from the group consisting of substantially homogenous ceramic oxides, substantially homogenous ceramic carbides, substantially homogenous ceramic borides, substantially homogenous ceramic nitrides, nitrogen-hardened titanium, and nitrided cobalt chrome.

11. The surgical cutting block of claim 10 wherein the material is selected from the group consisting of zirconia, alumina and nitrogen hardened titanium.

12. The surgical cutting block of claim 11 wherein the material is zirconia.

* * * * *